United States Patent [19]

Gerster et al.

[11] Patent Number: 5,266,575
[45] Date of Patent: Nov. 30, 1993

[54] 2-ETHYL 1H-IMIDAZO[4,5-C]QUINOLIN-4-AMINES

[75] Inventors: John F. Gerster, Woodbury; Charles E. Weeks, White Bear Township, Ramsey County, both of Minn.

[73] Assignee: Minnesota Mining and Manufacturing Company, St. Paul, Minn.

[21] Appl. No.: 788,565

[22] Filed: Nov. 6, 1991

[51] Int. Cl.⁵ .................... C07D 471/14; A61K 31/44
[52] U.S. Cl. ....................................... 514/293; 546/82
[58] Field of Search ........................... 546/82; 514/293

[56] References Cited

U.S. PATENT DOCUMENTS 4,689,338  8/1987  Gerster ............................... 514/293

FOREIGN PATENT DOCUMENTS 190109  2/1988  Hungary .

Primary Examiner—C. Warren Ivy
Assistant Examiner—Phyllis G. Spivack
Attorney, Agent, or Firm—Gary L. Griswold; Walter N. Kirn; Douglas E. Reedich

[57] ABSTRACT

2-Ethyl 1H-imidazo[4,5-c]quinolin-4-amines, which are active as immunomodulators and antiviral agents, and intermediates in the preparation of such compounds, pharmaceutical compositions and pharmacological methods of use.

3 Claims, No Drawings

2-ETHYL 1H-IMIDAZO[4,5-C]QUINOLIN-4-AMINES

BACKGROUND OF THE INVENTION

1. Field of the Invention

This invention relates to 1H-imidazo[4,5-c]quinoline compounds. In other aspects, this invention relates to 1H-imidazo[4,5-c]quinolin-4-amines, intermediates for the preparation of such compounds, pharmaceutical compositions containing such compounds, and pharmacological methods of using such compounds. This invention also relates to methods of inducing biosynthesis of tumor necrosis factor.

2. Description of the Related Art

The first reliable report of the 1H-imidazo[4,5-c]quinoline ring system, Backman et al., J. Org. Chem. 15, 1278-1284 (1950), describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines have been reported. For example, Jain et al., J. Med. Chem. 11, pp. 87–92 (1968), has synthesized the compound 1-[2-(4-piperidyl)ethyl]1H-imidazo[4,5-c]quinoline as a possible anticonvulsant and cardiovascular agent. Also, Baranov et al., Chem. Abs. 85, 94362 (1976), has reported several 2-oxoimidazo[4,5-c]quinolines, and Berenyi et al., J. Heterocyclic Chem. 18, 1537-1540 (1981), has reported certain 2-oxoimidazo[4,5-c]-quinolines.

Certain antiviral 1H-imidazo[4,5-c]quinolin-4amines are described in U.S. Pat. No. 4,689,338 (Gerster). These compounds are substituted on the 1-position by alkyl, hydroxyalkyl, acyloxyalkyl, benzyl, phenylethyl or substituted phenylethyl, and at the 2-position with hydrogen, alkyl, benzyl, or substituted benzyl, phenylethyl or phenyl. Furthermore, these compounds are known to induce interferon biosynthesis. Other antiviral 1H-imidazo[4,5-c]quinolin-4-amines, substituted on the 1-position by alkenyl substituents, are described in U.S. Pat. No. 4,929,624 (Gerster).

U.S. Pat. No. 4,698,348 (Gerster) discloses 1H-imidazo[4,5-c]quinolines that are active as bronchodilators, such as 4-substituted 1H-imidazo[4,5-c]quinolines wherein the 4-substituent is, inter alia, hydrogen, chloro, alkylamino, or dialkylamino, and the 2-substituent is, inter alia, hydroxyalkyl, aminoalkyl, or alkanamidoalkyl. Said patent also discloses 3-amino and 3-nitro quinoline intermediates substituted at the 4-position by hydroxyalkylamino or cyclohexylmethylamino, and 1H-imidazo[4,5-c]quinoline N-oxide intermediates substituted at the 2-position with, inter alia, hydroxyalkyl, aminoalkyl, or alkanamidoalkyl.

Tumor necrosis factor (TNF) is an endogenic glycoprotein that has the capability to selectively destroy tumor cells. For this reason there is considerable interest in TNF as a cancer therapeutic agent.

Biosynthesis of tumor necrosis factor has been induced by immunomodulators such as interleukin-2, and by catabolic enzymes such as those disclosed in European Patent Application 0,421,023A (Ransberger et al.).

DETAILED DESCRIPTION OF THE INVENTION

This invention provides compounds of Formula I:

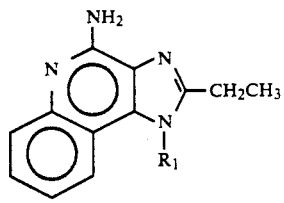

wherein $R_1$ is 2-methylpropyl or 2-hydroxy-2-methylpropyl.

This invention also provides intermediate compounds of Formula II:

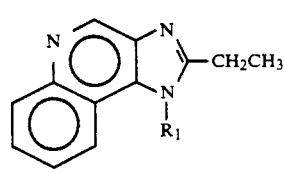

wherein $R_1$ is defined above.

This invention also provides intermediate compounds of Formula III:

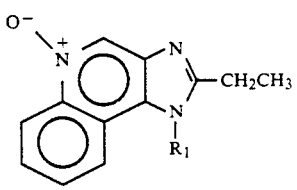

wherein $R_1$ is as defined above.

The compounds of the invention can be prepared as set forth in the Examples below.

A compound of Formula I can be used in the form of a free base or it can be used in the form of a pharmaceutically acceptable acid-addition salt such as a hydrochloride, dihydrogen sulfate, trihydrogen phosphate, hydrogen nitrate, methanesulfonate or a salt of another pharmaceutically acceptable acid. A pharmaceutically acceptable acid-addition salt of a compound of Formula I can be prepared by reaction of the compound with an equimolar amount of a relatively strong acid, preferably an inorganic acid such as hydrochloric, sulfuric, or phorsphoric acid, or an organic acid such as methanesulfonic acid, in a polar solvent. Isolation of the salt is facilitated by the addition of a solvent, such as diethyl ether, in which the salt is insoluble.

The compounds of Formula I can be utilized to achieve a desired pharmacological effect by administration to a patient in an appropriately formulated pharmaceutical composition. Suitable pharmaceutical compositions comprise a pharmaceutically acceptable carrier and a therapeutically effective amount of a compound of Formula I. The amount or concentration of a compound of Formula I that constitutes a therapeutically effective amount will depend of course on the particular desired pharmacological effect, on the route of administration, and on the particular formulation being used. Suitable therapeutically effective amounts can be selected by those skilled in the art.

Suitable pharmaceutical compositions include those suitable for oral, parenteral (including subcutaneous, intramuscular, intraperitoneal, and intravenous), buccal, rectal, or transdermal administration, or administration by inhalation.

Pharmaceutical compositions for oral administration can take the form of tablets, capsules, suspensions, solutions, or emulsions. Tablets can comprise pharmaceutically acceptable excipients such as diluents, binding agents, lubricants, disintegrants, flavors, colors, and the like. Liquid preparations can be prepared by conventional means with pharmaceutically acceptable excipients such as suspending agents, emulsifying agents, vehicles, preservatives, colors, sweetening agents, and the like. Compositions for oral administration can be formulated to give controlled release of the active compound by use of suitable pharmaceutically acceptable polymers.

Pharmaceutical compositions for parenteral administration can take the form of solutions, suspensions, or emulsions in aqueous or oily vehicles and can comprise pharmaceutically acceptable excipients such as buffering agents, tonicity adjusters, suspending agents, emulsifiers, and the like.

Pharmaceutical compositions for buccal administration can take the form of tablets or lozenges. Alternatively, the active compound can be incorporated into a transmucosal delivery device. Transmucosal delivery devices can comprise a backing and a matrix containing the active compound, a buccal adhesive, and optionally a penetration enhancer.

Pharmaceutical compositions for rectal administration can take the form of suppositories prepared by combining the active compound with conventional suppository bases.

Pharmaceutical compositions for transdermal administration can take the form of creams or lotions comprising pharmaceutically acceptable excipients such as ointment bases, oils, preservatives, emulsifiers, skin penetration enhancers, and the like. Alternatively, the active compound can be incorporated into a transdermal delivery device. The transdermal delivery device can be in the form of a bandage comprising a backing layer, a reservoir containing the active compound, optionally with other excipients, optionally a rate controlling membrane, and means for securing the device to the skin. Alternatively, the transdermal delivery device can comprise a backing layer with an adhesive matrix containing the active compound and optionally one or more excipients.

Pharmaceutical compositions for administration by inhalation can take the form of solutions, suspensions, or powders that can be delivered by means of a pressurized aerosol container or a nebulizer.

The compounds of Formula I exhibit antiviral activity in mammals. They can therefore be used to control viral infections. For example, a compound of Formula I can be used as an agent to control infections in mammals caused by Type II Herpes simplex virus. Compounds of Formula I can also be used to treat a herpes infection by oral, topical, or intraperitoneal administration.

The compounds of Formula I were tested and found to induce biosynthesis of interferon in human cells. The test methods and results are set forth below. These results suggest that compounds of the invention might be useful in treating other diseases such as rheumatoid arthritis, warts, eczema, Hepatitis B, psoriasis, multiple sclerosis, essential thrombocythaemia, cancer such as basal cell carcinoma, and other neoplastic diseases.

The compounds of Formula I have been shown by the test methods set forth below to induce biosynthesis of tumor necrosis factor (TNF) in human cells. Moreover, the compounds of Formula I induce TNF biosynthesis when administered at lower dose concentrations than structurally related compounds of the prior art. Thus the compounds of Formula I have potential as cancer therapeutic agents e.g., for local (e.g., topical, rectal, vaginal) administration or aerosol administration.

In the following Examples, the particular materials and amounts thereof recited as well as other conditions and details, should not be construed to unduly limit the invention.

EXAMPLE 1

2-Ethyl-1-(2-methylpropyl)-1H-imidazo[4,5-c]quinoline

A 16.55 g (0.077 mol) portion of $N^4$-(2-methylpropyl)-3,4-quinolinediamine (U.S. Pat. No. 4,689,338 example 16) was suspended in 100 mL of propionic acid and then heated at 120° C. for about 20 hours. After cooling to room temperature, the reaction mixture was poured into 300 mL of water, made basic with concentrated ammonium hydroxide, cooled in an ice bath and then extracted with diethyl ether. The volume of the ether extract was reduced under vacuum. The resulting precipitate was collected, rinsed with ether and dried to provide 11 g of crystalline solid, m.p. 72–73.5° C. Analysis: Calculated for $C_{16}H_{19}N_3$: %C, 75.8; %H, 7.6; %N, 16.6; Found: %C, 75.6; %H, 7.7; %N, 16.5.

EXAMPLE 2

2-Ethyl-1-(2-methylpropyl)-1H-imidazo[4,5-c]quinoline 5N Oxide

A 9.92 mL portion of peracetic acid was added to a solution of 10.65 g (0.042 mol) of 2-ethyl-1-(2-methylpropyl)-1H-imidazo[4,5-c]quinoline in 100 of ethyl acetate. The mixture was heated at reflux for about 2 hours and then cooled to room temperature. A precipitate was collected, rinsed with ethyl acetate and dried to provide 4 g of a yellow solid, m.p. 177°–180° C. This material was used without further purification.

EXAMPLE 3

2-Ethyl-1-(2-methylpropyl)-1H-imidazo[4,5-c]quinolin-4-amine

A 3.7 g (0.014 mol) portion of 2-ethyl-1-(2-methylpropyl)-1H-imidazo[4,5-c]quinoline 5N oxide was suspended in 35 mL of methylene chloride, cooled in an ice bath and then combined with 45 mL of chilled ammonium hydroxide. The resulting two phase mixture was stirred vigorously with cooling in an ice bath while a solution of 2.87 g (0.015 mol) of tosyl chloride in 30 mL of methylene chloride was slowly added. The reaction mixture was allowed to slowly warm to room temperature with stirring. The methylene chloride was evaporated to provide an orange solid which was collected, rinsed with water and air dried. The solid was then recrystallized from methylene chloride containing a trace of methanol to provide 2.7 g of a white solid, m.p. 233°–234° C. Analysis: Calculated for $C_{16}H_{20}N_4$: %C, 71.6; %H, 7.5; %N, 20.9; Found: %C, 71.3; %H, 7.3; %N, 20.6.

EXAMPLE 4

α,α-Dimethyl-2-ethyl-1H-imidazo[4,5-c]quinoline-1-ethanol

A mixture containing 15.4 g (0.067 mol) of 1-[(3-amino-4-quinolinyl)amino]-2-methyl-2-propanol (U.S. Pat. No. 4,689,338 example 189) and 14.5 mL (0.07 mol) of triethyl orthopropionate was heated at about 165° C. for about 2 hours. The resulting solid was slurried in a mixture of ethyl acetate and ether, collected and dried to provide 15.2 g of a solid. This material was used without further purification.

EXAMPLE 5

2-Ethyl-1-(2-hydroxy-2-methylpropyl)-1H-imidazo[4,5-c]quinoline 5N Oxide

Using the general method of Example 2, 15.2 g of α,α-dimethyl-2-ethyl-1H-imidazo[4,5-c]quinoline-1-ethanol was oxidized to provide 15.2 g of crude N oxide. A sample was dissolved in water then precipitated by the addition of sodium hydroxide. The precipitate was collected and dried to provide a solid, m.p. 245°–250° C. Analysis: Calculated for $C_{16}H_{19}N_3O_2 + \frac{1}{2} H_2O$: %C, 65.3; %H, 6.8; %N, 14.3; Found: %C, 65.2; %H, 6.4; %N, 14.0.

EXAMPLE 6

4-Amino-α,α-dimethyl-2-ethyl-1H-imidazo[4,5-c]quinoline-1-ethanol

Using the general method of Example 3, 14.3 g (0.05 mol) of 2-ethyl-1-(2hydroxy-2-methylpropyl)-1H-imidazo[4,5-c]quinoline 5N oxide was aminated to provide 8.2 g of crude product. This material was recrystallized from 60 mL of ethanol to provide 6.4 g of solid, m.p. 222°–225° C. Analysis: Calculated for $C_{16}H_{20}N_4O$: %C, 67.6; %H, 7.1; %N, 19.7; Found: %C, 67.6; %H, 7.1; %N, 19.7.

COMPARATIVE EXAMPLE C1

4-Amino-α,α,2-trimethyl-1H-imidazo[4,5-c]quinoline-1-ethanol

A mixture containing 1.5 g (0.0056 mol) of 1-[(3-amino-2-chloro-4-quinolinyl)amino]-2-methyl-2-propanol (U.S. Pat. No. 4,988,815 example 13), 1.4 g (0.0085 mol) of triethyl orthoacetate and 4 mL of xylenes was heated at 135°–140° C. for 6 hours. The solution was evaporated to provide a beige oil comprising 4-chloro-α,α,2-trimethyl-1H-imidazo[4,5-c]quinoline-1-ethanol which was used without further purification.

The crude material was combined with 15 mL of 15% methanolic ammonia and heated in a steel bomb at about 150° C. for 7 hours. The reaction mixture was partially evaporated then diluted with a small amount of water. The resulting precipitate was collected, rinsed sequentially with methanol, water, then methanol and dried to provide 900 mg of crude product. The crude product was recrystallized from methanol/methylene chloride to provide 500 mg of colorless crystals, m.p. 290°–293° C. Analysis: Calculated for $C_{15}H_{18}N_4O$: %C, 66.6; %H, 6.7; %N, 20.7; Found: %C, 66.6; %H, 6.7; %N, 20.6.

COMPARATIVE EXAMPLE C2

2-Methyl-1-(2-methylpropyl)-1H-imidazo[4,5-c]quinolin-4-amine

This compound can be prepared by known methods. See for example U.S. Pat. No. 4,689,338 example 113.

COMPARATIVE EXAMPLE C3

1-(2-Methylpropyl)-1H-imidazo[4,5-c]quinolin-4-amine

This compound can be prepared by known methods. See for example U.S. Pat. No. 4,689,338 example 99 or U.S. Pat. No. 4,988,815 example 10.

COMPARATIVE EXAMPLE C4

4-Amino-α,α-dimethyl-1H-imidazo[4,5-c]quinoline-1-ethanol

This compound can be prepared by known methods. See for example U.S. Pat. No. 4,689,338 example 189.

The 2-ethyl 1H-imidazo[4,5-c]quinolin-4-amines of the invention and comparative compounds were tested according to the methods set forth below:

TUMOR NECROSIS FACTOR (α) INDUCTION IN HUMAN CELLS

This test method is an assay for tumor necrosis factor (α) induction in human mononuclear cells in culture. Activity is based on the measurement of human tumor necrosis factor (α) secreted into culture medium. Human tumor necrois factor (α) is measured by radioimmunoassay.

Blood Cell Preparation for Culture

Whole blood is collected by venipuncture into EDTA ($K_3$) vacutainer tubes. Peripheral blood mononuclear cells (PBM's) are prepared by Leuco-PREP TM Brand Cell Separation Tubes (available from Becton Dickinson Labware, Lincoln Park, N.J.) and cultured in RPMI 1640 medium (available from GIBCO, Grand Island, N.Y.) supplemented with 25 mM HEPES (N-2-hydroxyethylpiperazine-N'-2-ethanesulfonic acid) and L-glutamine with 1% penicillin-streptomycin solution added) with 10% autologous serum (heat inactivated, 56° C. for 30 minutes) added. 200 μL portions of PBM's in medium are added to 96 well (flat bottom) MicroTest TM III tissue culture plates (available from Falcon Plastics, Oxnard, Calif.).

Compound Preparation

Test compounds are solubilized in water, ethanol or dimethyl sulfoxide then diluted with distilled water, 0.01N sodium hydroxide or 0.01N hydrochloric acid (The choice of solvent will depend on the chemical characteristics of the compound being tested.). It is preferred that the final concentration of ethanol or dimethylsulfoxide, if used, does not exceed 1%. Compounds are intially tested in a concentration range of about 0.5 μg/mL to about 5 μg/mL. Compounds which show induction at a concentration of 0.5 μg/mL are then tested in a concentration range of 0.01 μg/mL to 0.5 μg/mL/.

Incubation

The solution of test compound is added in a predetermined volume (less than or equal to 50 μL) to the wells containing 200 μL of PBM's in medium. Solvent and/or medium is added to control wells (i.e., wells containing no test compound) and as needed to the test wells in order to adjust the final volume of each well to 250 µL. The plates are covered with plastic lids, vortexed gently and then incubated for 18 hours at 37° C. with a 5% carbon dioxide atmosphere.

Separation

Following incubation, the plates are covered with PARAFILM TM laboratory film and then centrifuged at 1000 rpm for 15 minutes at 4° C. in a Damon IEC Model CRU-5000 centrifuge. Medium (about 200 µL) is removed from 4 to 8 wells and pooled into 2 mL sterile freezing vials. Samples are maintained at −70° C. until analysis.

Tumor necrosis factor (α) analysis/calculation

Tumor necrosis factor (α) is measured using an Enzyme Immuno Assay (available from Biosource International, California). Results are expressed as picograms/mL based on a standard curve conducted for each assay. Lipopolysaccharide, a known inducer of tumor necrosis factor (α), is included in each assay and is used to provide a comparison of response for each culture and assay. Lipopolysaccharide has been evaluated in this test method over a range 0.01 to 5 µg/mL and typically gives a response of 1000 to 3000 picograms/mL.

RESULTS

The compounds of the invention and comparative compounds were screened side-by-side in two separate assays. The results are shown in Tables 1 and 2. The blood used to run the assay of Table 1 was obtained from a different donor than that used to run the assay of Table 2.

TABLE 1

TUMOR NECROSIS FACTOR (α) INDUCTION IN HUMAN CELLS TNF (α) (picograms/mL)

| Compound of Example | Dose Concentration (µg/mL) | | | |
|---|---|---|---|---|
| | 0.5 | 1.0 | 5.0 | Solvent |
| 3 | 1109 | 1519 | 1274 | DMSO |
| 6 | 950 | 1938 | 3740 | DMSO |
| C1 | 438 | 653 | 2186 | DMSO |
| C2 | 617 | 849 | 1203 | DMSO |
| C3 | 235 | 302 | 380 | water |
| C4 | 671 | 295 | 607 | water |
| LPS | 2580 | 2681 | 2648 | water |
| Control | 90 | | | |

TABLE 2

TUMOR NECROSIS FACTOR (α) INDUCTION IN HUMAN CELLS TNF (α) (picograms/mL)

| Compound of Example | Dose concentration (µg/mL) | | | | |
|---|---|---|---|---|---|
| | 0.01 | 0.05 | 0.1 | 0.5 | Solvent |
| 3 | 19 | 126 | 408 | 1742 | DMSO |
| 6 | 26 | 94 | 262 | 1554 | DMSO |
| C1 | 17 | 48 | 43 | 613 | DMSO |
| C2 | 35 | 44 | 46 | 1076 | DMSO |
| C3 | 15 | 51 | 39 | 53 | water |
| C4 | 25 | 32 | 37 | 39 | water |
| LPS | 1620 | 1840 | 1812 | 1799 | water |
| Control | 42 | | | | |

The results in TABLES 1 and 2 show that the compounds of Examples 3 and 6 induce biosynthesis of TNF in human cells when administered at lower dose concentrations than structurally related compounds of the prior art.

INTERFERON (α) INDUCTION IN HUMAN CELLS

An in vitro human blood cell system was used to assess interferon induction by compounds of the invention. Activity is based on the measurement of interferon secreted into culture medium. Interferon is measured by bioassay.

Blood Cell Preparation for Culture

Whole blood is collected by venipuncture into EDTA vacutainer tubes. Peripheral blood mononuclear cells (PBM's) are prepared by LeucoPREP TM Brand Cell Separation Tubes (available from Becton Dickinson) and cultured in RPMI 1640 medium (available from GIBCO, Grand Island, N.Y.) supplemented with 25 mM HEPES (N-2-hydroxyethylpiperazine-N'-2-ethanesulfonic acid) and L-glutamine (1% penicillin-streptomycin solution added) with 10% autologous serum (heat inactivated, 56° C. for 30 minutes) added. 200 µL portions of PBM's in medium are added to 96 well (flat bottom) MicroTest TM III tissue culture plates (available Falcon Plastics).

Compound Preparation

The compounds are solubilized in water, ethanol or dimethyl sulfoxide then diluted with distilled water, 0.01N sodium hydroxide or 0.01N hydrochloric acid (The choice of solvent will depend on the chemical characteristics of the compound being tested.). Compounds are intially tested in a concentration range of from about 0.1 µg/mL to about 5 µg/mL. Compounds which show induction at a concentration of 0.5 µg/mL are then tested in a concentration range of 0.01 µg/mL to 5.0 µg/mL/.

Incubation

The solution of test compound is added in a volume (less than or equal to 50 µL) to the wells containing 200 µL of PBM's in medium. Solvent and/or medium is added to control wells (i.e., wells containing no test compound) and as needed to the test wells in order to adjust the final volume of each well to 250 µL. The plates are covered with plastic lids, vortexed gently and then incubated for 24 hours at 37° C. with a 5% carbon dioxide atmosphere.

Separation

Following incubation, the plates are covered with PARAFILM TM laboratory film and then centrifuged at 1000 rpm for 15 minutes at 4° C. in a Damon IEC Model CRU-5000 centrifuge. Medium (about 175 µL) is removed from 4 to 8 wells and pooled into 2 mL sterile freezing vials. Samples are maintained at −70° C. until analysis.

Interferon Analysis/Calculation

Interferon is determined by bioassay using A549 human lung carcinoma cells challenged with encephalomyocarditis. The details of the bioassay method have been described by G. L. Brennan and L. H. Kronenberg in "Automated Bioassay of Interferons in Micro-test Plates", Biotechniques, June/July; 78, 1983., incorporated herein by reference. Briefly stated the method is as follows: interferon dilutions and A549 cells are incubated at 37° C. for 12 to 24 hours. The incubated cells are infected with an inoculum of encephalomyocarditis virus. The infected cells are incubated for an additional period at 37° C. before quantifying for viral cytopathic effect. The viral cytopathic effect is quantified by staining followed by spectrophotometric absorbance measurements. Results are expressed as (α) reference units/mL based on the value obtained for NIH HU IF-L standard. The interferon was identifed as essentially all interferon (α) by testing in checkerboard neutralization assays against rabbit antihuman interferon (β) and goat anti-human interferon (α) using A549 cell monolayers challenged with encephalomyocarditis virus.

RESULTS

Results are shown in Table 3 wherein the absence of an entry indicates that the compound was not tested at the particular dose concentration. Results designated as "<" a certain number indicate that interferon was not detectable in amounts above the lower sensitivity level of the assay.

TABLE 3
INTERFERON (α) INDUCTION IN HUMAN CELLS

| Compound of Example | Reference units/mL Dose concentration (μg/mL) | | | | | |
|---|---|---|---|---|---|---|
| | 0.01 | 0.05 | 0.1 | 0.5 | 1.0 | 5.0 |
| 3 | 37 | 1200 | 190 | 1100 | 1000 | 640 |
| 6 | 4.3 | 67 | 110 | 150 | 150 | 110 |
| C1 | 4.2* | 406* | 619* | 493* | 557* | 557* |
| C2 | <1.8 | 140 | 250 | 750 | 750 | 750 |
| C3 | | | 10.5* | 340* | 550* | 296* |
| C4 | | | <6.4 | <6.4 | 1200 | 1200 |

*Average of the values obtained in three separate assays.

The results shown in TABLE 3 show that the compounds of Examples 3 and 6 induce biosynthesis of interferon in human cells.

ANTIVIRAL ACTIVITY IN GUINEA PIGS

The test methods described below demonstrate the ability of compounds of the invention to reduce the number and severity of lesions developed by guinea pigs infected with Type II Herpes simplex virus.

Female Hartley guinea pigs weighing 200 to 250 g are anesthetized with methoxyflurane (available under the tradename Metafane from Pitman-Moore, Inc., Washington Crossing, N.J.), after which the vaginal area is swabbed with a dry cotton swab. The guinea pigs are then infected intravaginally with a cotton swab saturated with Herpes simplex virus Type II strain 333 ($1 \times 10^5$ plaque forming units/mL). Guinea pigs are assigned to groups of 7 animals; one group for each treatment and one to serve as a control (vehicle treated). The compounds of the invention are formulated in water containing 5% Tween 80 (a polyoxyethylene sorbitan monooleate available from Aldrich Chemical Company, Inc., Milwaukee, Wis.). The guinea pigs are treated orally once daily for four consecutive days starting 24 hours after infection.

Antiviral activity is evaluated by comparing lesion development in compound treated versus vehicle treated guinea pigs. External lesions are scored 4, 7, 8 and 9 days after infection using the following scale: 0—no lesion, 1—redness and swelling, 2—a few small vesicles, 3—several large vesicles, 4—large ulcers with necrosis and 5—paralysis. The maximum lesion score of each guinea pig is used to calculate the percentage lesion inhibition. The percentage lesion inhibition is calculated as follows:

$$100 - \frac{\text{Sum of maximum lesions scores of treat group}}{\text{Sum of maximum lesion scores of vehicle group}} \times 100$$

Results are shown in Table 4.

TABLE 4
ANTIVIRAL ACTIVITY IN GUINEA PIGS

| Compound of Example | Dose mg/Kg | % Lesion Inhibition |
|---|---|---|
| 3 | 0.3 | 56 |
| 3 | 0.1 | 13 |
| 3 | 0.03 | 37 |
| 6 | 1 | 100 |
| 6 | 0.5 | 100 |
| 6 | 0.3 | 93 |
| 6 | 0.1 | 0 |
| C1 | 0.5 | 100 |
| C1 | 0.1 | 50 |
| C2 | 2 | 100 |
| C3 | 3 | 96 |
| C3 | 2 | 56* |
| C3 | 1 | 14 |
| C4 | 1 | 100 |

*Average value from three separate assays

The results in TABLE 4 show that the compounds of Examples 3 and 6 reduce the number of lesions developed by guinea pigs infected with the Type II Herpes simplex virus.

We claim:

1. A compound of the formula:

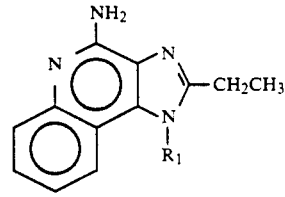

wherein $R_1$ is 2-methylpropyl or 2-hydroxy-2-methylpropyl, or a pharmaceutically acceptable acid addition salt thereof.

2. An antiviral pharmaceutical composition comprising a compound according to claim 1 and a pharmaceutically acceptable vehicle, the compound being present in an amount effective to inhibit and/or prevent the progress of a viral infection.

3. A method of inducing tumor necrosis factor biosynthesis in a mammal, which method comprises administering to the mammal a compound according to claim 1 in an amount sufficient to induce tumor necrosis factor biosynthesis.

* * * * *